United States Patent [19]
Chin et al.

[11] Patent Number: 5,599,297
[45] Date of Patent: Feb. 4, 1997

[54] APPARATUS AND METHOD FOR DELIVERING INSUFFLATION GAS AND LOCAL ANESTHESIA TO A BODY CAVITY

[75] Inventors: Albert K. Chin, Palo Alto; Phillip K. Hopper, San Carlos, both of Calif.

[73] Assignee: Origin Medsystems, Inc., Menlo Park, Calif.

[21] Appl. No.: 408,699

[22] Filed: Mar. 21, 1995

Related U.S. Application Data

[63] Continuation of Ser. No. 39,975, Mar. 30, 1993, Pat. No. 5,399,159.

[51] Int. Cl.$^6$ .................................................. A61M 37/00
[52] U.S. Cl. .................................................. 604/26; 604/49
[58] Field of Search .................................. 604/23, 26, 49, 604/51, 54, 244, 246; 128/200.14, 200.21, 200.23, 200.24, 203, 12

[56] References Cited

U.S. PATENT DOCUMENTS

| | | | |
|---|---|---|---|
| 375,015 | 12/1887 | Smith . | |
| 391,546 | 10/1888 | Mess . | |
| 662,658 | 11/1900 | Sterne | 604/26 |
| 3,425,414 | 2/1969 | LaRoche | 128/201 |
| 3,688,765 | 9/1972 | Gasaway | 604/143 |
| 3,867,941 | 2/1975 | Lindemann | 604/23 |
| 3,982,533 | 9/1976 | Wiest | 128/184 |
| 4,177,814 | 12/1979 | Knepshield et al. | 604/26 |
| 4,342,310 | 8/1982 | Lindemayer et al. | 604/70 |
| 4,454,877 | 6/1984 | Miller et al. | 128/200.21 |
| 4,464,169 | 8/1984 | Semm | 604/26 |
| 4,852,561 | 8/1989 | Sperry | 128/200.83 |
| 4,867,212 | 9/1989 | Mohr et al. | 141/290 |
| 4,874,362 | 10/1989 | Wiest et al. | 604/26 |
| 4,966,578 | 10/1990 | Baier et al. | 604/26 |
| 5,137,478 | 8/1992 | Freitas | 604/26 |
| 5,139,478 | 8/1992 | Konicky et al. | 604/23 |
| 5,209,721 | 5/1993 | Wilk | 604/26 |
| 5,226,876 | 7/1993 | Filipi et al. | 604/26 |
| 5,246,419 | 9/1993 | Absten | 604/26 |
| 5,299,565 | 4/1994 | Brown | 128/200.21 |
| 5,411,474 | 5/1995 | Ott et al. | 604/26 |

Primary Examiner—John D. Yasko
Attorney, Agent, or Firm—Limbach & Limbach L.L.P.

[57] ABSTRACT

A hand-held apparatus and method for insufflating an abdominal cavity includes a compact gas supply unit comprised of a gas cartridge which has a pair of tandem piercable seals positioned inside the cartridge neck and which contains a predetermined mass of compressed gas. A cap having a puncture stem is engaged with the gas supply unit, causing the puncture stem to penetrate the piercable seals and release gas through the puncture tube and into a hollow needle positioned inside the abdomen. The tandem piercable seals are arranged such that as the gas supply unit is engaged with the cap, the puncture stem punctures the first piercable seal and the first piercable seal seals around it before the puncture stem punctures the second piercable seal, thereby preventing accidental loss of gas and preserving the entire mass of gas for insufflation. Gas loss may be further prevented by a compression seal or an elastomeric diaphragm which provides a leakproof seal between the cap and the neck when the cap and gas supply unit are engaged. An anesthesia attachment provides for administration of an anesthetic liquid in combination with the insufflation gas.

7 Claims, 12 Drawing Sheets

APPARATUS AND METHOD FOR DELIVERING INSUFFLATION GAS AND LOCAL ANESTHESIA TO A BODY CAVITY

This is a continuation of application Ser. No. 08/039,975, filed Mar. 30, 1993, now U.S. Pat. No. 5,399,159.

FIELD OF THE INVENTION

The present invention relates to a gas insufflator and, more particularly, is concerned with a hand-held insufflator for use in a medical office or emergency room.

BACKGROUND OF THE INVENTION

A gas insufflator is a device used to inflate the abdominal cavity. Insufflation of the cavity is necessary to provide a working space for a surgeon to examine the contents of the cavity or operate within the cavity. Insufflating the abdominal cavity with gas, normally carbon dioxide, elevates the abdominal wall and pushes the contents of the region, such as the bowel and the liver, away from the areas of the cavity requiring the surgeon's attention.

Various gas insufflators for use in the operating room are known. These insufflators infuse between 4 and 6 liters of carbon dioxide into the abdomen, creating a distention pressure of 15 mmHg (0.33 psi). Their flow rates range from 3 liters per minute to 15 liters per minute.

The carbon dioxide for the operating room units is supplied by large pressurized tanks. Flow rate and pressure may be regulated by controls located on the insufflator units, and monitors located on the units display gas flow rate, gas pressure, and the total infusion volume. These devices are large and cumbersome and therefore inconvenient for use in a doctor's office or emergency room. In these settings, it is desirable to have a compact hand-held insufflation unit. Such a simplified unit would lack most of the controls and instrumentation provided in an operating room insufflation unit, but would have to provide an adequate volume of insufflation gas without the risk of over insufflation.

OBJECTS AND SUMMARY OF THE INVENTION

A principal object of the present invention is to provide an insufflator which is sufficiently compact and portable to be used in an office or emergency room.

A further object of the present invention is to provide a compact insufflator which will create sufficient distention of the abdominal cavity to allow for examination and manipulation of the abdominal contents, bowel, and organs without the risk of over insufflation.

Another object of the present invention is to prevent accidental gas loss from the insufflator, so that a predetermined volume of insufflation gas can be delivered into the abdominal cavity from a predetermined mass of compressed gas stored in a detachable gas cartridge.

The present invention provides a compact hand-held insufflation unit primarily intended for diagnostic use in a physician's office or emergency room. The unit delivers a predetermined volume of insufflation gas into the abdominal cavity from a one-time use gas cartridge that holds a predetermined mass of compressed gas. The predetermined volume of insufflation gas, approximately 2.5 liters of carbon dioxide, is sufficient to provide partial insufflation of the abdominal cavity without the risk of over insufflation, regardless of body habitus. The amount of insufflation provided is sufficient to permit examination of the abdominal contents and limited manipulation of the bowel and abdominal organs, but cannot cause over-distension of the abdomen.

The hand-held insufflation unit according to the invention comprises a cap and a gas supply unit which is engaged with the cap, normally immediately prior to the insufflation unit being used. The gas supply unit includes a tubular cartridge housing that holds the gas cartridge. The gas cartridge is sealed with a pierceable seal.

An axial bore in the cap has a puncture stem on one end, and includes a flow restrictor which limits the flow rate of insufflation gas to about 3 liters per minute. When the cap and gas supply unit are engaged, the puncture stem pierces the pierceable seal in the gas cartridge and compressed gas can flow out of the gas cartridge.

An outlet line is attached to the other end of the axial bore in the cap. The outlet line feeds insufflation gas into the abdominal cavity via a pneumoneedle or Veress needle inserted laparoscopically in the abdominal cavity. The outlet line includes a control valve, which is operated by the surgeon to start and stop the flow of insufflation gas. The outlet line may also include a flow gauge to assist the surgeon in determining whether the needle tip has been inserted into the correct intra-abdominal space. Flow of greater than 1 liter per minute generally indicates that the needle tip lies properly inside the abdomen rather than in the muscle, properitoneal fat layer, or properitoneal space.

In one embodiment of the invention, the outlet line additionally includes an anesthetic vial and spray tube which provide an atomized spray of an anesthetic drug in combination with the gas. Insufflation using the anesthetic/gas combination prevents discomfort caused by insufflation.

Because of the need to deliver the predetermined volume of insufflation gas into the abdomen from the predetermined mass of compressed gas in the gas cartridge, the hand-held insufflation unit according to the invention includes several measures to prevent or detect any leakage of compressed gas that would otherwise reduce the predetermined volume of insufflation gas delivered into the abdomen.

Compressed gas can leak from the gas cartridge while the gas cartridge is in storage before the gas supply unit is engaged with the cap. To detect such leakage, the tubular cartridge housing has an open end that is covered by an elastomeric diaphragm. Distention of, or a break in, the elastomeric diaphragm indicates a gas supply unit that has leaked in storage or has previously been used and which therefore should not be used. The elastomeric diaphragm also protects the gas cartridge from inadvertent puncture by the puncture stem during storage and transportation.

Compressed gas can leak from the gas cartridge via the connection between the gas cartridge and the puncture stem as the gas supply unit is engaged with the cap. To prevent such leakage, the gas cartridge is preferably provided with two pierceable seals in tandem. The tandem piercable seals are arranged such that as the gas supply unit is engaged with the cap, the puncture stem punctures the first piercable seal and the first piercable seal seals around it before the puncture stem punctures the second piercable seal. A suitably recessed single piercable seal can be used instead of tandem piercable seals, but the latter arrangement gives better protection against in-storage leakage.

As an alternative or additional means for preventing gas leaks, the cap may be provided with a compression seal. The compression seal forms a seal with a portion of the gas cartridge surrounding the pierceable seals as the gas supply unit and cap are engaged. Another gas-tight seal is created between the cap, the elastomeric diaphragm, and the neck of the cartridge as the gas supply unit and cap are engaged. The tandem piercable seals, the compression seal, and the elastomeric diaphragm provide duplicative seals against leakage, and the use of any of them alone could be sufficient to prevent such leakage.

BRIEF DESCRIPTION OF THE DRAWINGS

FIGS. 5A through 8C show cross-sectional partial side elevations of various embodiments of the sealing arrangements as the puncture stem is inserted into the gas cartridge.

FIGS. 12 and 13 are cross-sectional side elevations of the cap of second embodiment of the hand-held insufflator. In FIG. 12 the thumb lever and valve shuttle are in the on position and in FIG. 13 the valve shuttle and thumb lever are in the off position.

DESCRIPTION OF THE PREFERRED EMBODIMENT

FIGS. 1–4 show a first, preferred, embodiment of the present invention and FIGS. 11–15 show a second embodiment.

Figure 1:
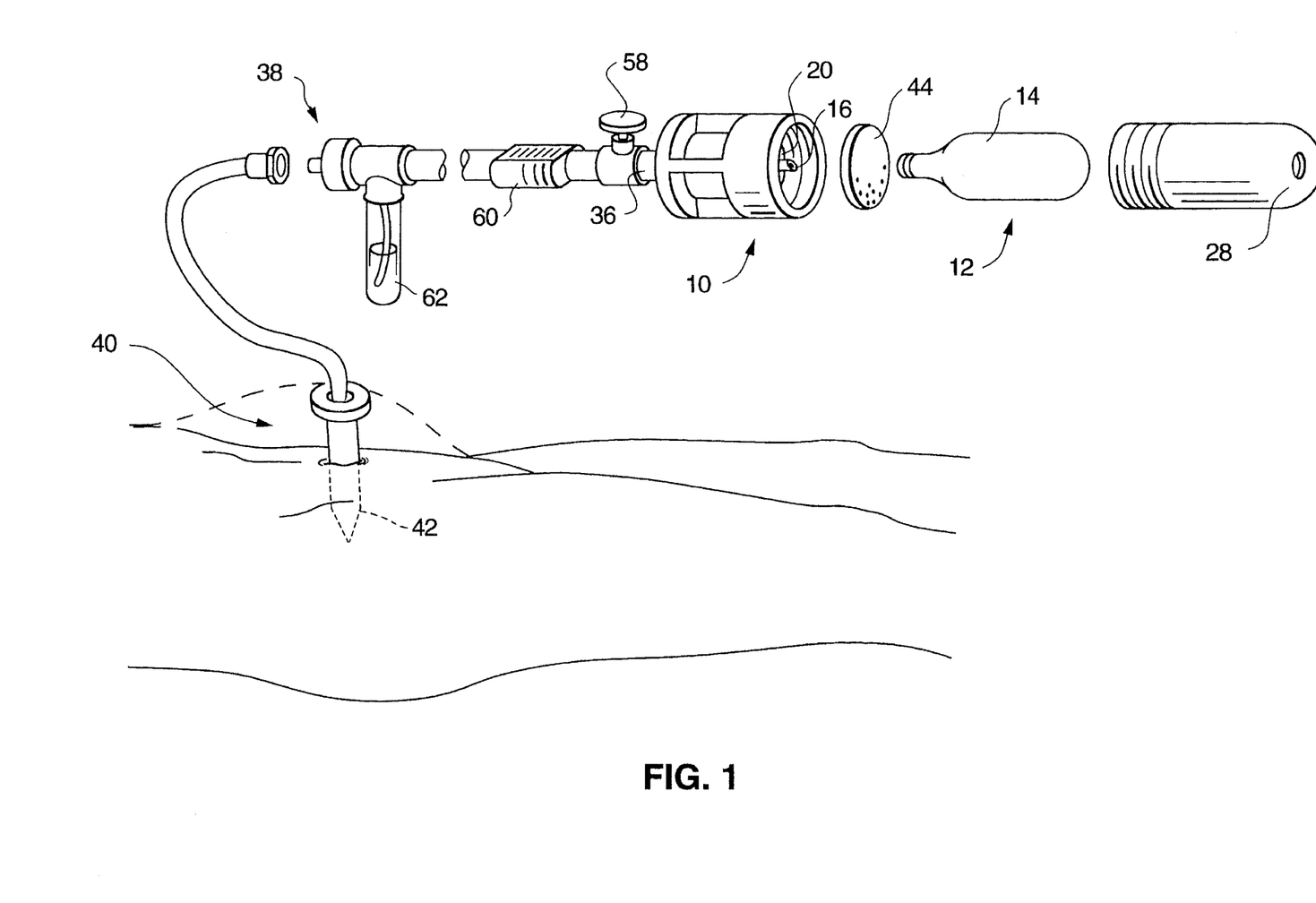
FIG. 1 is an exploded view of the hand-held insufflator and anesthesia assembly according to the invention.
Figure 2:
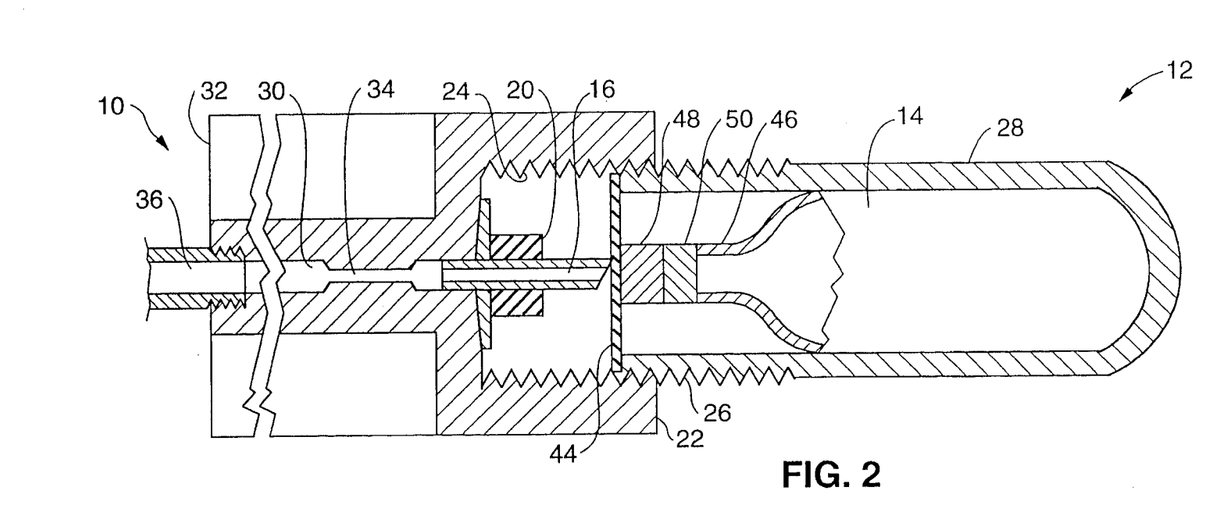
FIGS. 2, 3 and 4 are cross-sectional partial side elevations of the cap and gas supply unit of the hand-held insufflator according to the invention, showing the sequence of the puncture stem penetrating the sealing faces of the gas cartridge as the cap and the gas supply unit are engaged.
Figure 3:
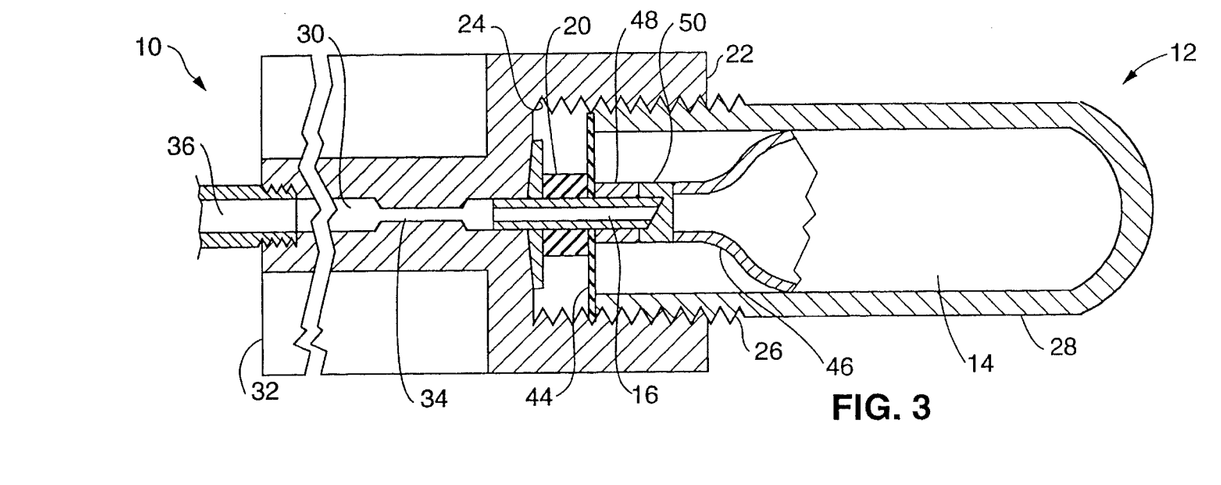
Figure 4:
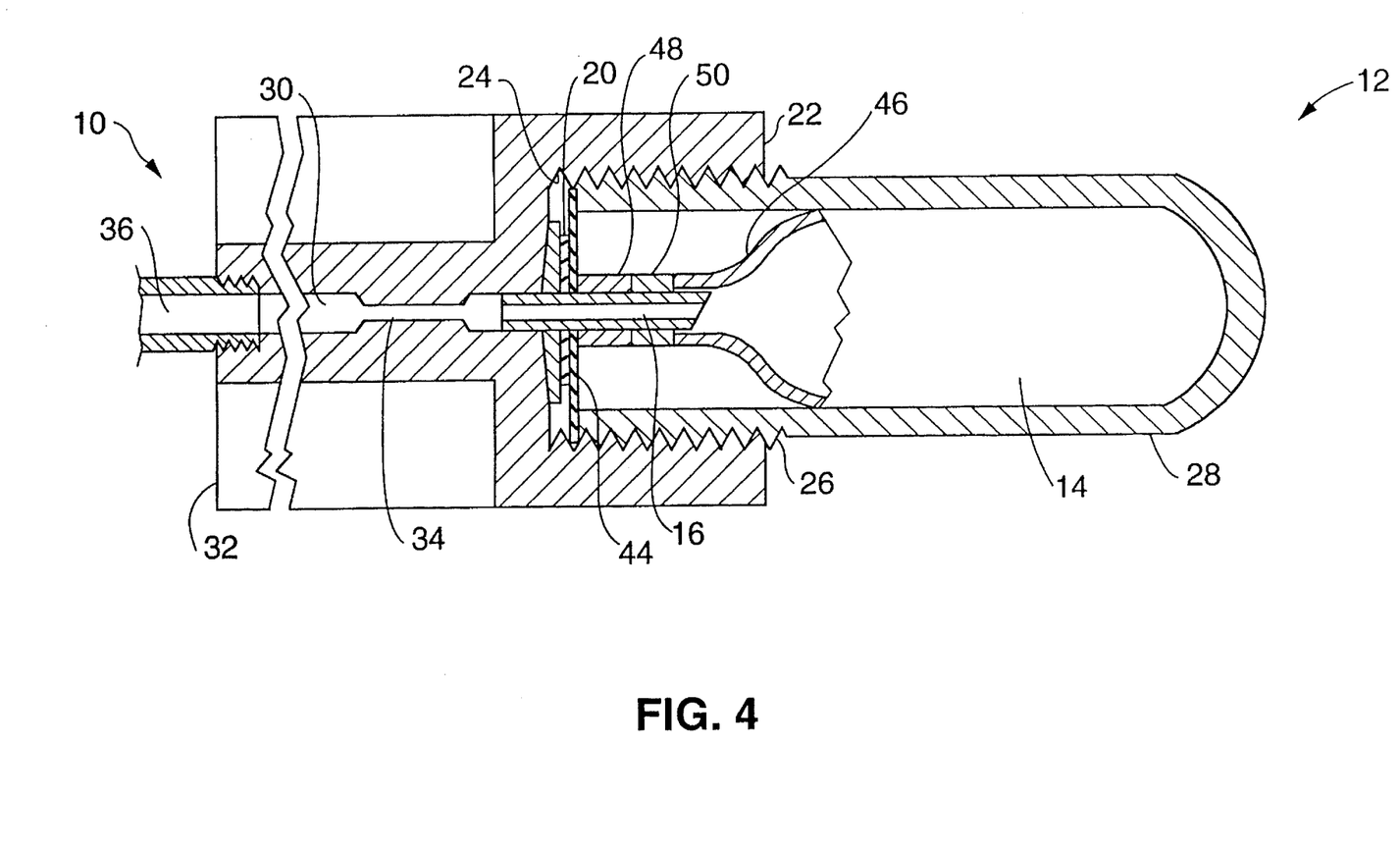

FIG. 1 shows an exploded view of the preferred embodiment of the hand-held insufflator according to the invention. Cross-sectional views of the preferred embodiment are shown in FIGS. 2, 3 and 4. Referring to these figures, the present invention is comprised generally of a cap 10 and a gas supply unit 12, which includes a gas cartridge 14 containing a predetermined mass of compressed gas. The cap 10 includes a puncture stem 16 which is preferably surrounded by an elastomeric compression seal 20. As will be described, the insufflation unit can only supply insufflation gas after the gas supply unit 12 has been screwed into the cap 10, causing the puncture stem 16 to advance and puncture the gas cartridge 14.

As shown in FIGS. 2 and 3, a threaded bore 24 is formed in the proximal face 22 of the cap 10. The threaded bore 24 is adapted to accept the threaded portion 26 on the outside of the tubular cartridge housing 28. The axial bore 30 interconnects the threaded bore 24 with the outer face 32 of the cap 10. The axial bore 30 includes a portion having a reduced diameter 34, which serves as a flow restrictor which restricts the flow of insufflation gas to about 3 liters/minute.

The puncture stem 16 is secured in the proximal end of the axial bore 30 such that the proximal end of the puncture stem projects from the distal end of the threaded bore 24 by a predetermined amount. The reasons for this will be discussed below.

The outlet line 36 forms a gas-tight connection with the distal end of the axial bore 30, and is connected via the optional anesthesia assembly 38 to a pneumoneedle or Veress needle 40 for insertion into the abdomen as shown in FIG. 1.

The puncture stem 16 is preferably surrounded by an elastomeric compression seal 20 which serves as a barrier against gas leakage. As will be discussed in detail below, the compression seal accomplishes this function by sealing against the neck of the gas cartridge when the cap and the gas supply unit are screwed together but before the sealing faces in the gas cartridge are completely punctured by the puncture stem.

FIG. 2 shows a cross-sectional side elevation of the gas supply unit 12. The gas supply unit 12 includes a tubular cartridge housing 28 which holds a gas cartridge 14 containing a predetermined mass of compressed insufflation gas.

The cartridge housing 28 has a threaded portion 26 adapted for engaging the threaded bore 24 of the cap 10. The preferred gas supply unit 12 is provided as a single, disposable, unit with the gas cartridge 14 sealed inside the cartridge housing 28 by an elastomeric diaphragm 44 across the open end of the cartridge housing. The elastomeric diaphragm 44 protects the gas cartridge 14 from accidental puncture during storage and transportation and keeps the gas cartridge 14 contained within the cartridge housing 28. The elastomeric diaphragm 44 also serves as a means for detecting whether some of the predetermined mass of gas in the gas cartridge has been lost due to leakage or use, enabling the surgeon to reject gas supply units which lack the full mass of insufflation gas. Distention of, or a break in the elastomeric diaphragm indicates a gas supply unit that has leaked in storage, or has previously been used, and which therefore should not be used. Alternatively, the cartridge housing may be reusable with disposable gas cartridges, however doing so eliminates the advantages provided by the elastomeric diaphragm.

The gas cartridge 14 contains a predetermined mass of insufflation gas. Carbon dioxide is the preferred insufflation gas because it is relatively non-reactive when released into the body. The predetermined mass of insufflation gas contained in the gas cartridge 14 is chosen such that it yields about 2.5 liters of insufflation gas at body temperature and a pressure of about 10 mm Hg above atmospheric. This corresponds to about 5 grams of carbon dioxide. To minimize the volume of the gas cartridge, the carbon dioxide is stored under a pressure sufficiently high to liquify it, such that it occupies a volume of about 2.5 cubic centimeters.

The gas cartridge 14 tapers into a substantially cylindrical neck 46 at one end. A pair of sealing faces 48 and 50 are mounted in tandem in the neck 46 so as to prevent the puncture stem 16 from releasing the gas through the sealing faces while the cap 10 and cartridge housing 28 are being engaged and after the sealing faces are punctured.

Various other sealing configurations may be employed to prevent any of the predetermined mass of gas from leaking after the puncture stem has penetrated the gas cartridge. These configurations preserve all of the predetermined mass of gas in the gas cartridge for insufflation. FIGS. 5A through 8C show four alternative embodiments as they are prepared for use by inserting the puncture stem into the gas cartridge. The descriptions of these embodiments are intended to be illustrative and are not an exclusive list of the embodiments encompassed by the present invention.

Figure 5A:
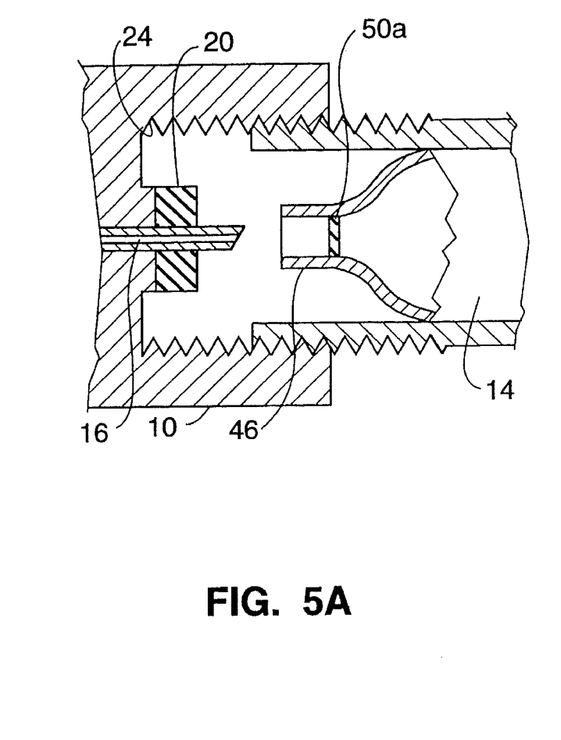
Figure 5B:
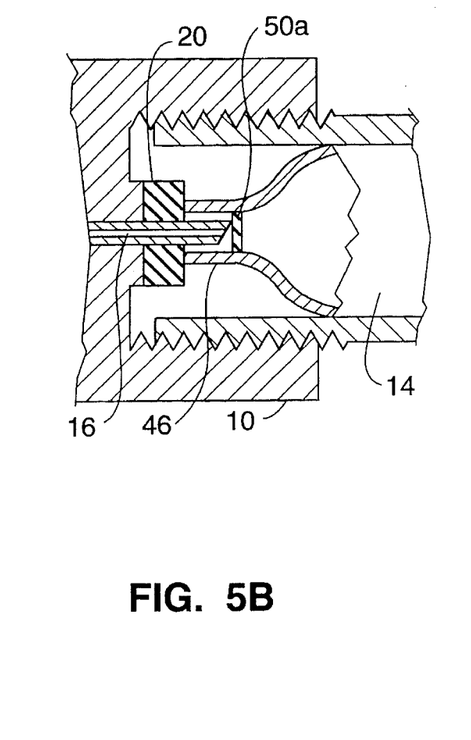
Figure 5C:
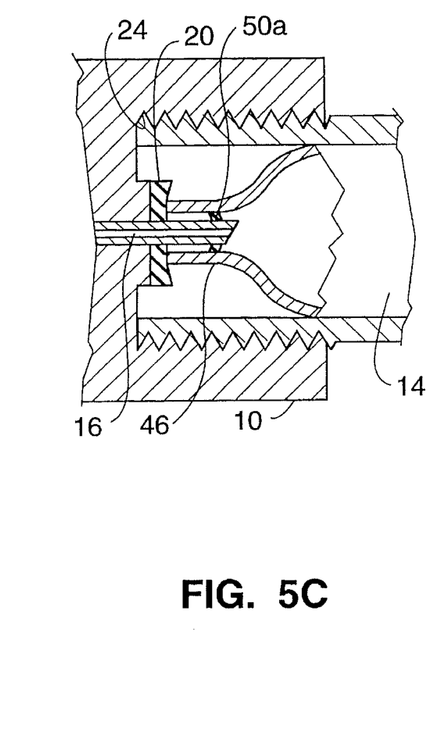
Figure 6A:
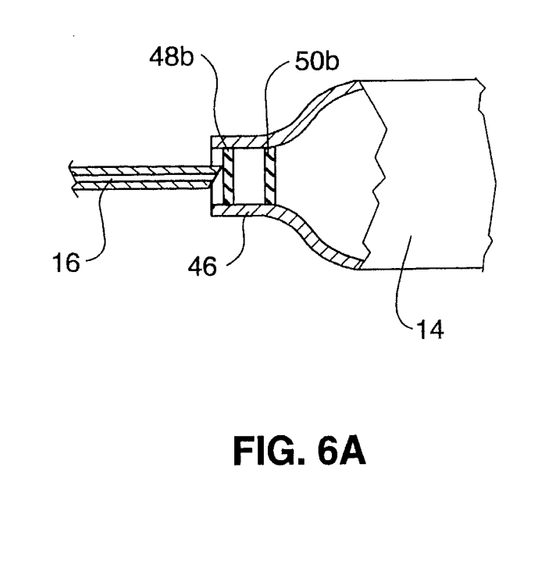
Figure 6B:
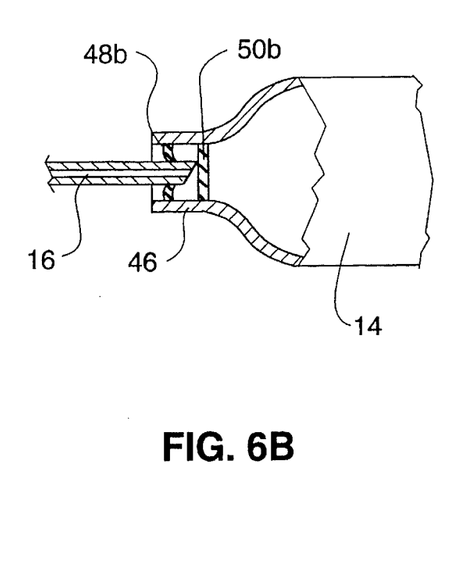
Figure 6C:
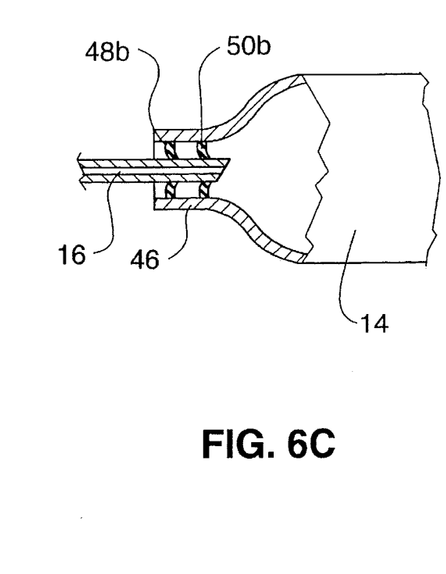

In the embodiment of FIGS. 5A, 5B, and 5C, the compression seal 20 which surrounds the puncture stem 16 in the cap 10 seals against the neck 46 of the gas cartridge 14 before the puncture stem 16 ruptures the sealing face 50a which is recessed in the neck 46. In the embodiment of FIGS. 6 & 6B, and 6C, the first sealing face 48b seals around the puncture stem 16 after the puncture stem 16 breaks through it and before the puncture stem 16 breaks through the second sealing face 50b which is recessed in the neck. A similar concept is employed in the third embodiment, shown in FIGS. 7A, 7B, and 7C. In this embodiment, the elastomeric diaphragm 44 serves the function of the first sealing face in the embodiment of FIG. 6A by sealing around the puncture stem 16 after the puncture stem ruptures the elastomeric diaphragm 44 and before it ruptures the recessed sealing face 50c in the neck 46.

Figure 7A:
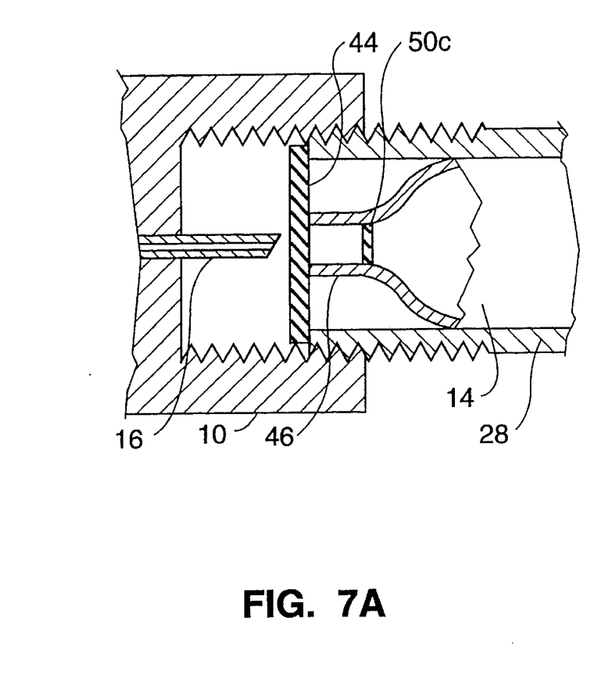
Figure 7B:
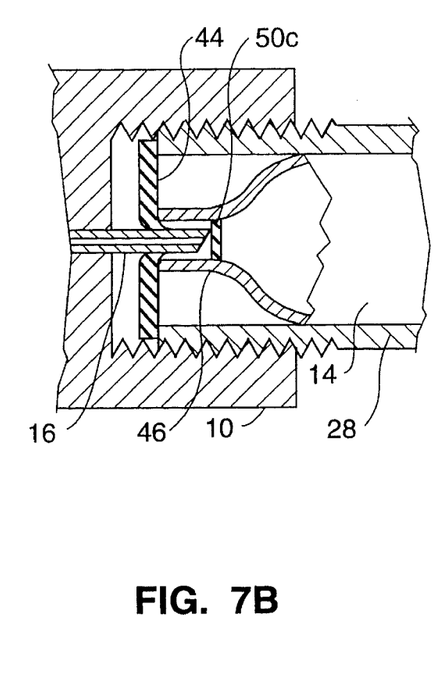
Figure 7C:
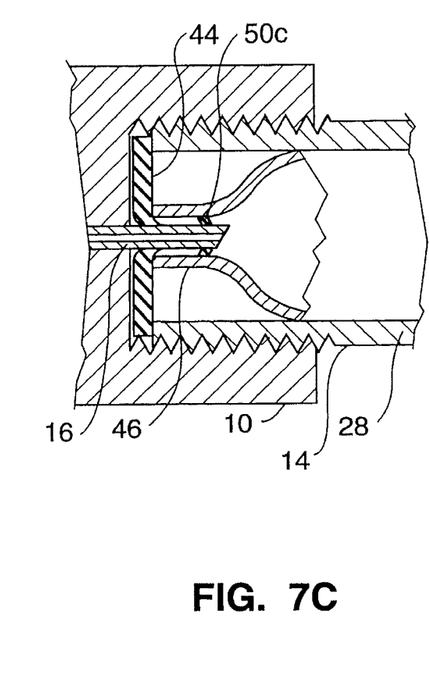
Figure 8A:
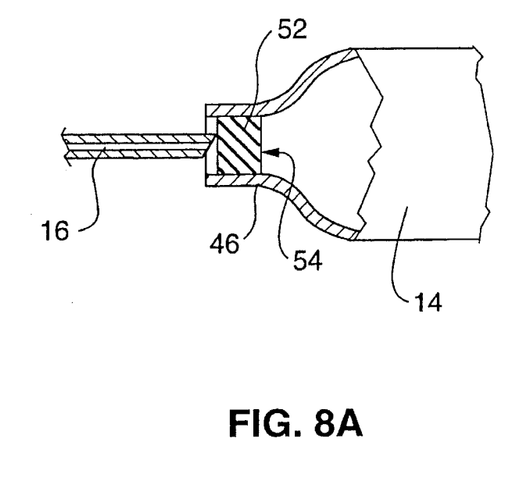
Figure 8B:
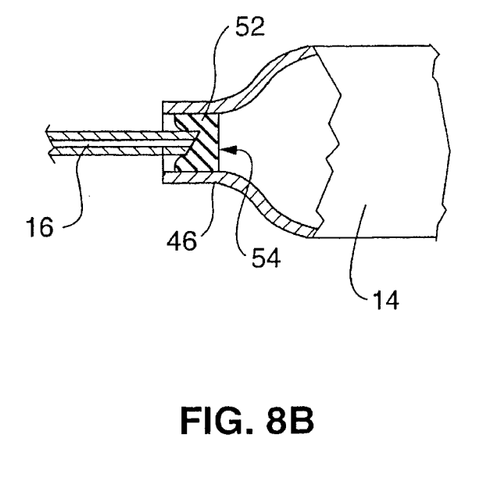
Figure 8C:
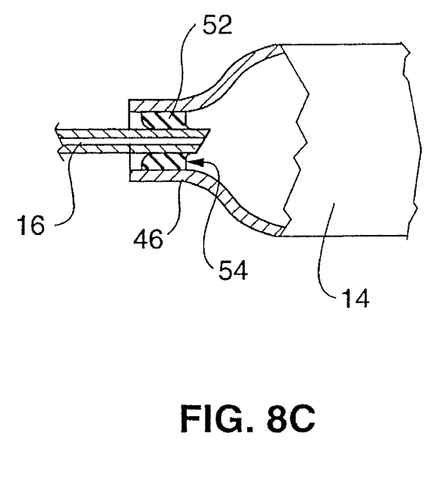

In the embodiment of FIGS. 8A and 8B, and 8C, one thick seal 52 seals the neck. The proximal portion 54 of the thick seal 52 seals around the puncture stem 16 once the puncture stem passes into the thick seal 52, thereby creating a seal around the puncture stem 16 before the puncture stem has completely ruptured the thick seal. An elastomeric diaphragm 44 as shown in FIG. 7A or a compression seal 20 as shown in FIG. 5A may also be used in combination with the embodiments shown in FIGS. 2, 6A, and 8A to provide added protection against gas leaks.

Operation of the hand-held insufflator will now be described with reference to FIGS. 1 through 4. Prior to use, the elastomeric diaphragm 44 of the gas supply unit 12 should be inspected for distension and for holes which would indicate that the gas cartridge 14 has leaked or been punctured. Gas supply units having distended or punctured diaphragms should be rejected as they may not allow sufficient distension of the abdominal cavity. Additionally, the user should ensure that the control valve 58 is closed prior to engaging the cap 10 and gas supply unit 12 so as to prevent gas from leaking from the outlet line after the seal on the gas cartridge is ruptured.

FIGS. 2, 3 and 4 show the preferred embodiment of the hand-held insufflator assembly as it is prepared for use. Hand-held insufflators with alternative embodiments of the gas cartridge are similarly prepared for use. The cap 10 and the cartridge housing 28 are threaded together at threaded portions 26 and 24. Engaging the cap 10 with the cartridge housing 28 linearly advances the puncture stem 16. The puncture stem 16 ruptures the elastomeric diaphragm 44 and then the first sealing face 48. The first sealing face 48 seals around the puncture stem 16 and thereby will prevent gas leaks when the puncture stem 16 penetrates the second sealing face 50. This prevents gas from leaking and ensures that the entire mass of gas in the gas cartridge is kept available for delivery into the abdominal cavity as insufflation gas.

Additional sealing is provided in the preferred embodiment because the pressure of the neck 46 against the elastomeric compression seal 20 creates a leak-proof seal before any gas is released from the gas cartridge (FIG. 3). If the gas supply unit includes an elastomeric diaphragm 44 across the opening in the cartridge housing, a leak-proof seal will be created when the elastomeric diaphragm 44 becomes sandwiched between the neck 46 of the gas cartridge and the compression seal 20. While the seals formed by the compression seal and/or elastomeric diaphragm provide added safeguards against leakage, they are not crucial in embodiments, such as the first embodiment, having double sealing faces which successfully avoid leaks.

After a leak-proof seal around the puncture stem and/or between the gas cartridge 14 and the cap 10 has been created, the puncture stem then advances through the second sealing face 50 (FIG. 4) as the cap 10 and cartridge housing 28 become completely engaged. Gas passes from the gas cartridge through the puncture stem and into the outlet line 36.

As shown in FIG. 1, a control valve 58 is located along the outlet line 36. The control valve 58 allows the surgeon to control the flow of gas through the outlet line 36. The control valve 58 is preferably a push-button valve as shown to allow one-handed operation of the insufflation unit. A flow gauge 60 may also be attached to the outlet line 36. The flow gauge aids the surgeon in determining if the pneumoneedle tip (not shown) has been inserted into the correct intra-abdominal space. A flow rate greater than 1 liter/minute generally indicates that the needle tip correctly lies inside the abdomen rather than in the muscle or properitoneal fat layer. It is preferable to include leak-proof seals (not shown), such as O-ring seals, at all junctions to prevent gas leaks.

Referring to FIG. 1, once the cap 10 and cartridge housing 28 are fully engaged and the pneumoneedle or Veress needle 40 is positioned in the abdominal cavity, the surgeon operates the control valve 58 to start and stop gas flow through the outlet line 36 and into the abdominal cavity via the pneumoneedle or Veress needle 40. If the flow gauge 60 indicates a flow rate of less than 1 liter/minute, the needle tip 42 may not be properly inside the abdomen and should be repositioned.

The outlet line 36 may include an anesthesia assembly 38. The anesthesia assembly 38 holds a supply of anesthetic liquid 62 such as Lidocaine, for spraying into the abdominal cavity along with the gas. Two embodiments for the anesthesia assembly are shown in FIGS. 9 and 10.

Figure 9:
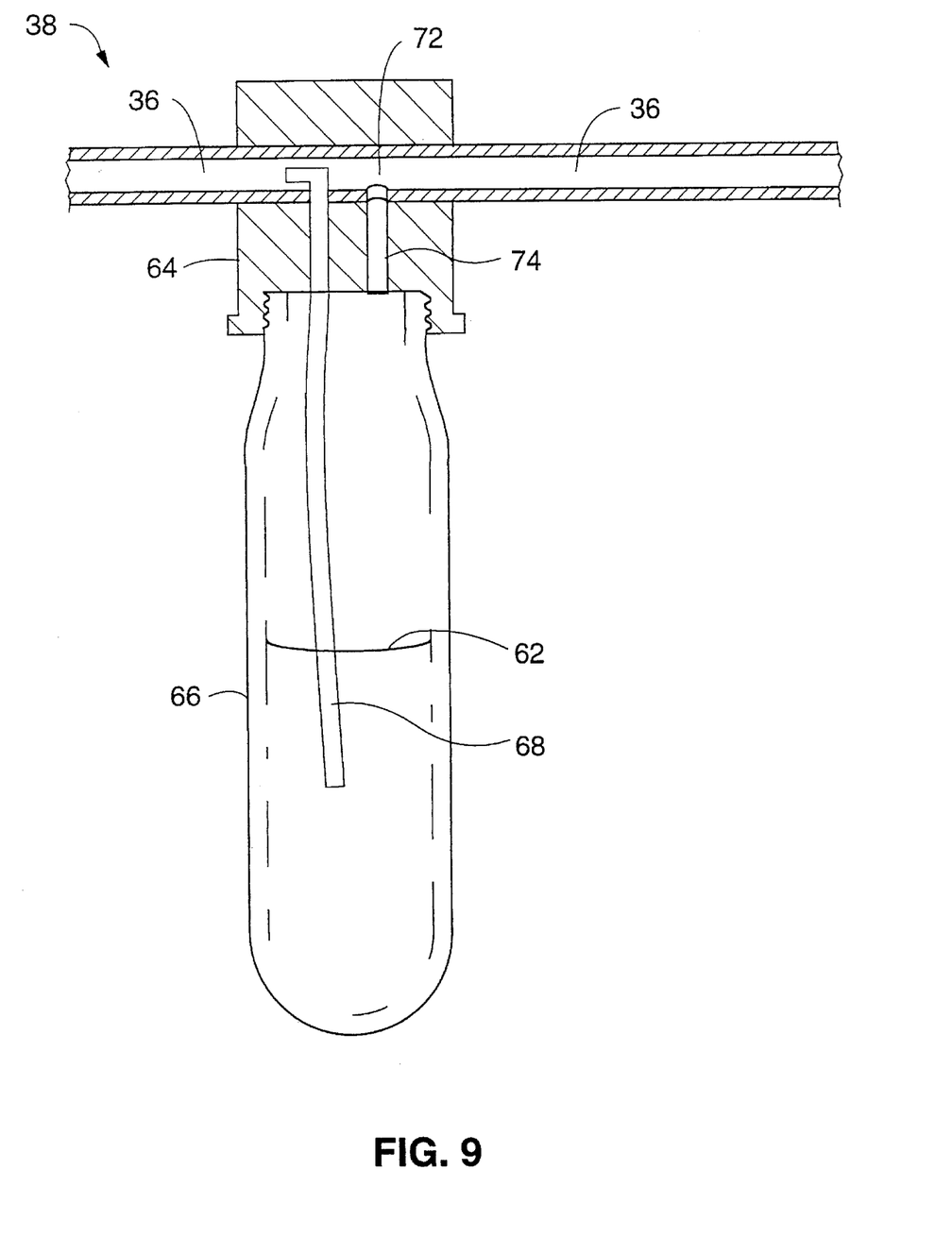
FIG. 9 is a cross-sectional side elevation of an anesthesia assembly of the hand-held insufflator according to the present invention.

FIG. 9 shows a cross-sectional side elevation of the first anesthesia assembly 38. The anesthesia assembly comprises an upper housing 64 and a vial 66 containing an anesthetic liquid 62 such as Lidocaine. A hollow spray tube 68 is mounted in the upper housing 64 and suspended into the vial 66. Both ends of the spray tube are open. One end of the spray tube 68 intersects with a bore 72 which passes through the upper housing 64 and which connects continuously with the outlet line 36. A channel 74 also passes from the bore 72 through the upper housing to the vial 66. The channel 74 applies gas pressure equal to the gas pressure in the bore 72 upstream of the spray tube to the surface of the liquid anesthetic in the vial 66. The difference between this pressure and the pressure in the bore 72 downstream of the spray tube 68 forces anesthetic up the spray tube and the anesthetic mixes with the gas passing through the bore 72. The anesthetic liquid combines with the gas to form an atomized mist which is carried through the pneumoneedle or Veress needle into the abdominal cavity.

Figure 10:
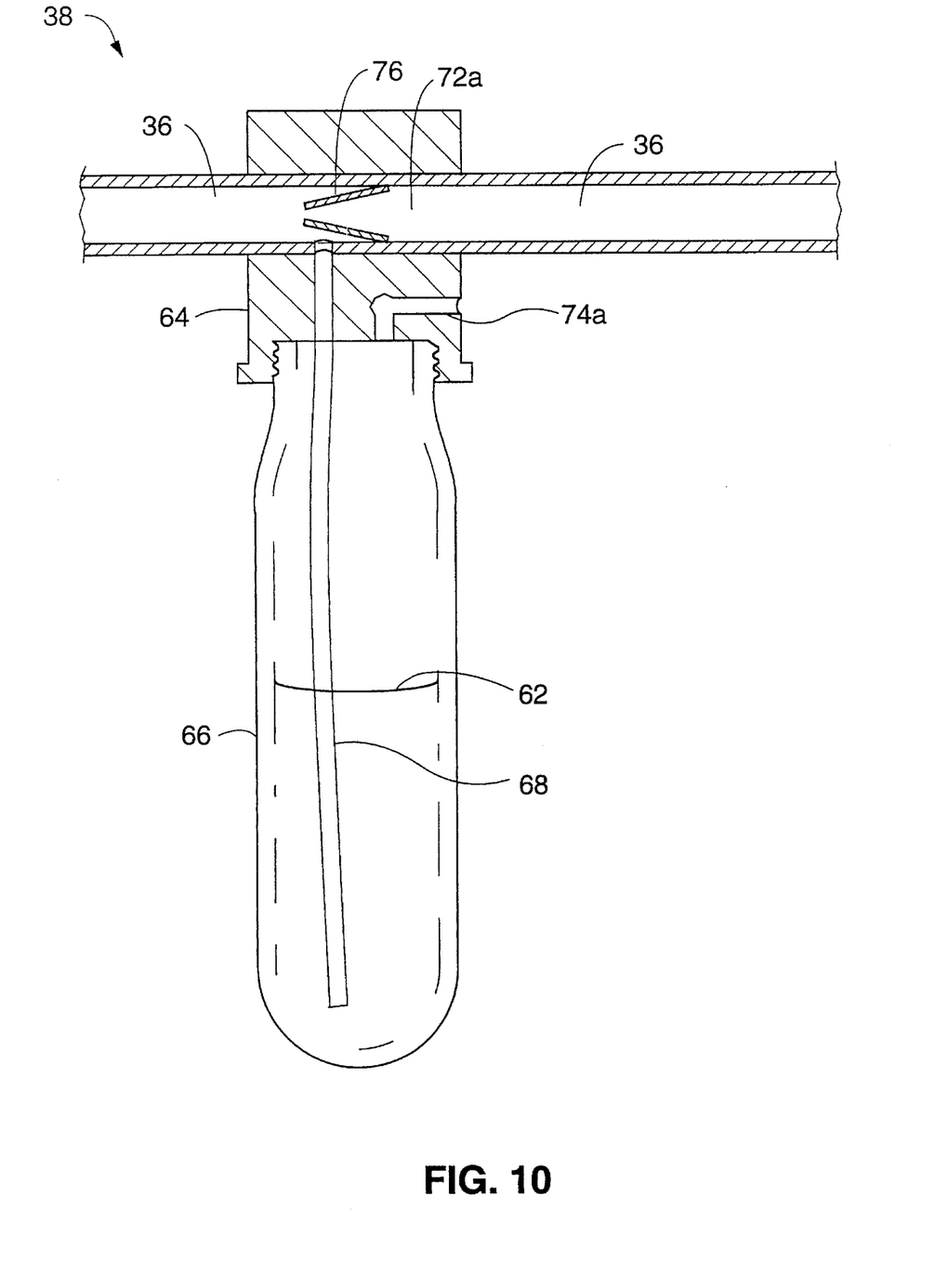
FIG. 10 is a cross-sectional side elevation of a second embodiment of the anesthesia assembly.

In the second embodiment of the anesthesia assembly 38, shown in FIG. 10, the insufflation gas passes through a venturi 76 after it moves from the outlet line 36 into the bore 72a. The channel 74a is open to the atmosphere. The pressure differential caused by the passage of gas through the venturi 76 draws the fluid up the spray tube 68. The anesthetic liquid combines with the gas to form an atomized mist which is carried through the pneumoneedle or Veress needle (not shown) into the abdominal cavity.

Figure 11:
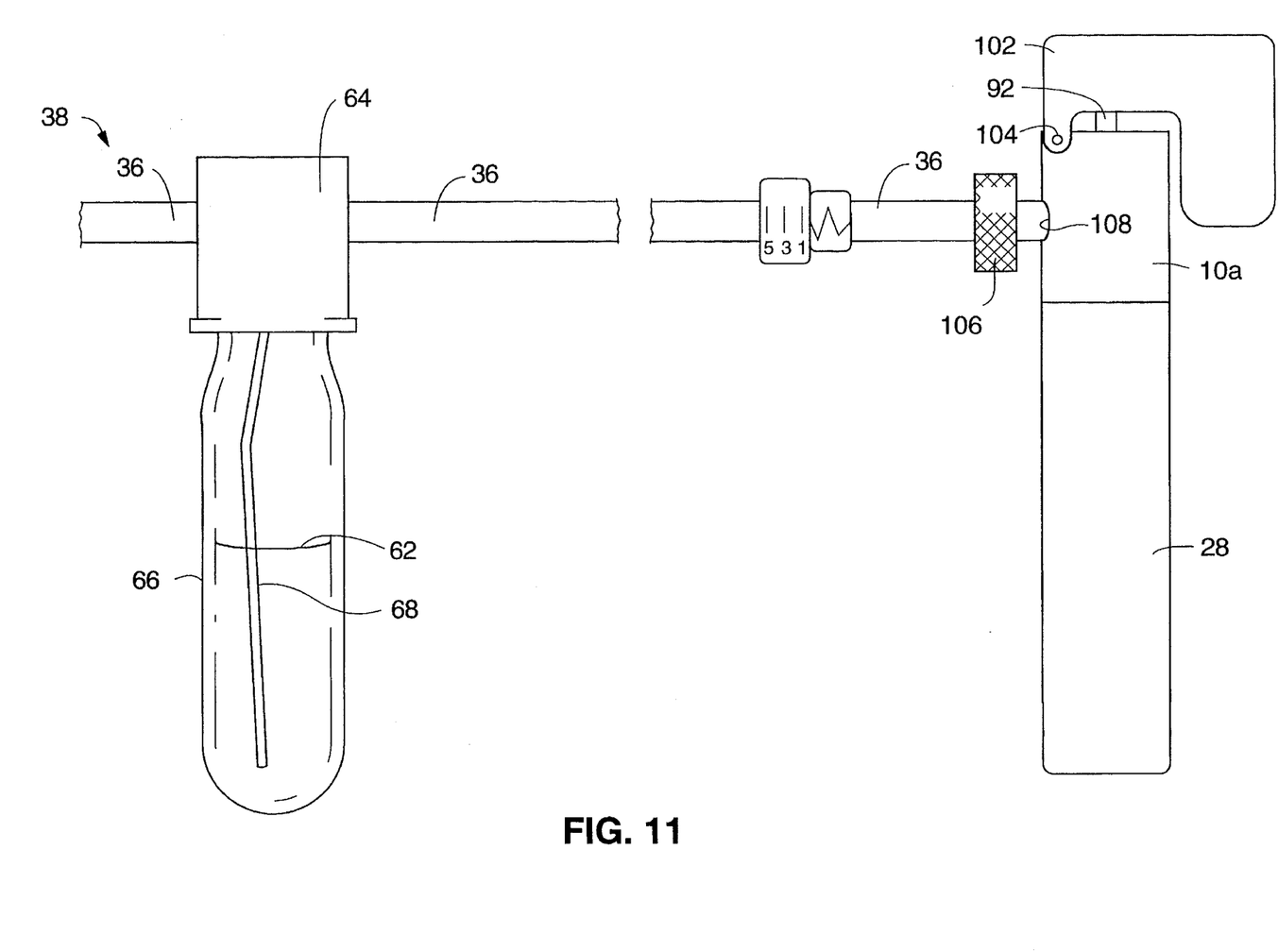
FIG. 11 is a side elevation of a second embodiment of the hand-held insufflator according to the present invention connected to the anesthesia assembly.
Figure 12:
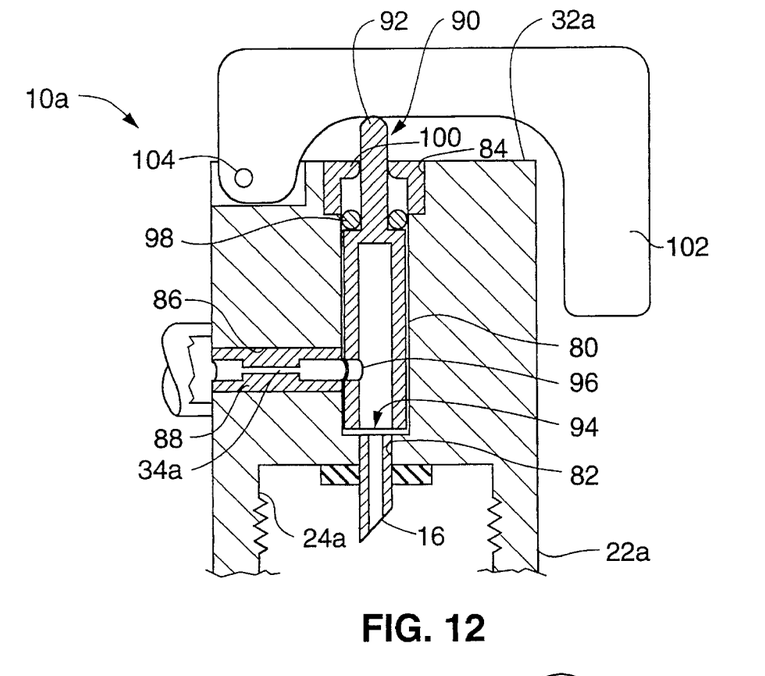
Figure 13:
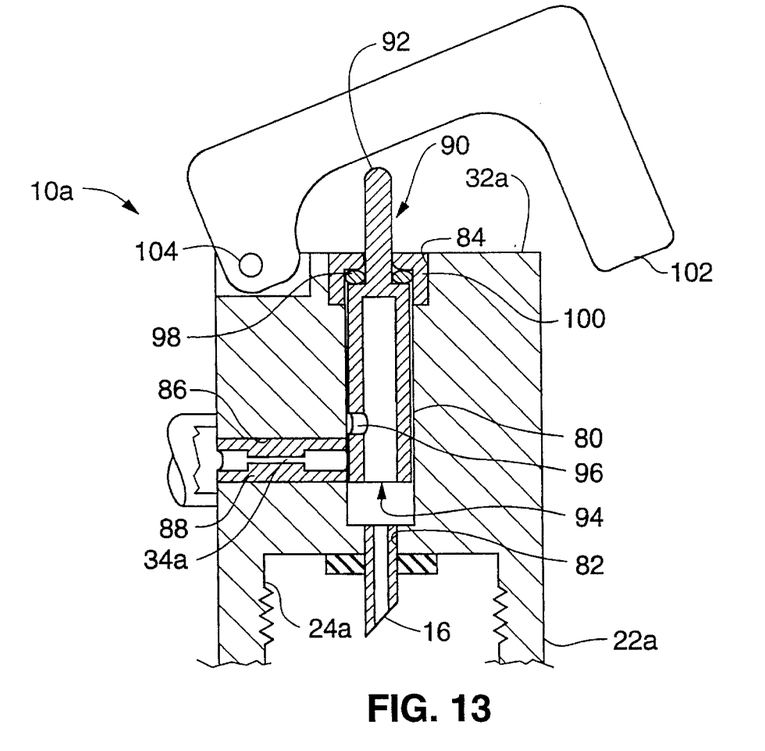
Figure 14:
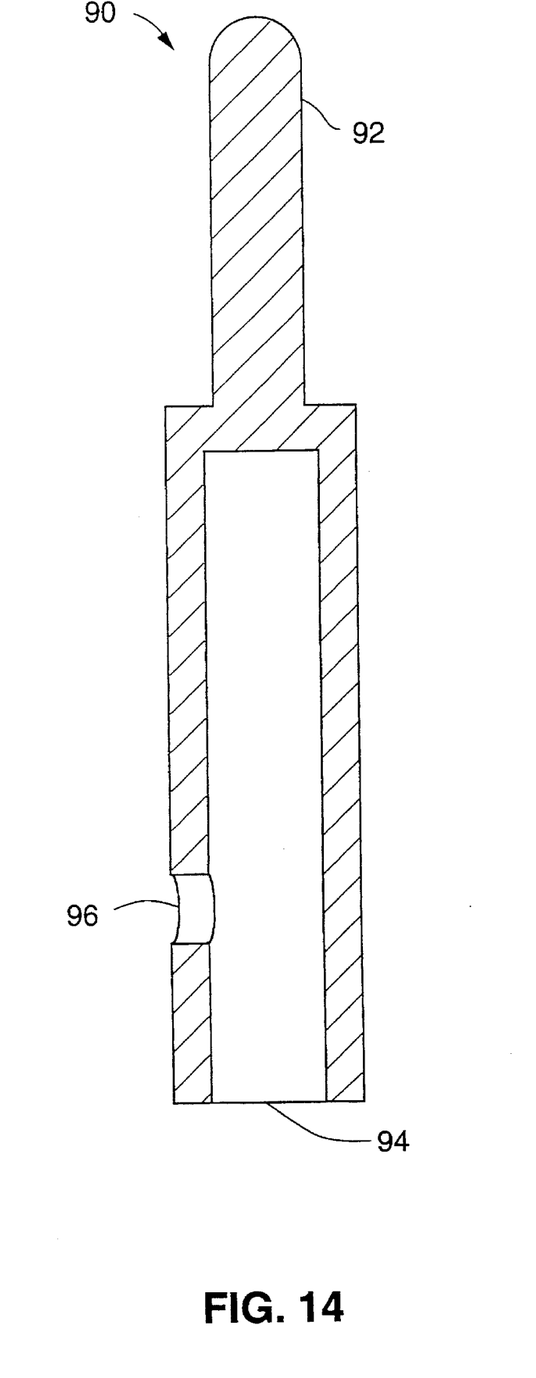
FIGS. 14 and 15 are a side elevation and a front elevation, respectively, of the valve shuttle of the second embodiment.
Figure 15:
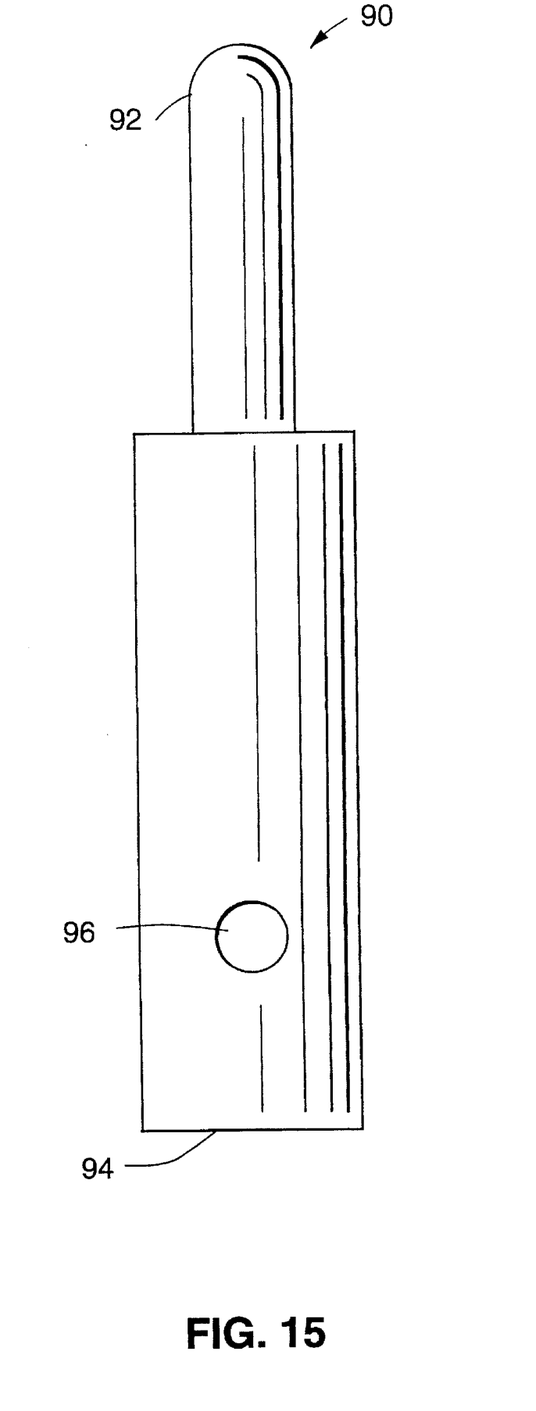

The second embodiment of the hand-held insufflator in which the control valve is built into the cap is shown in FIGS. 11 through 13. Referring to FIG. 12, a threaded bore 24a is formed in the proximal face 22a of the cap 10a. The threaded bore 24a is adapted to accept the threaded portion of the gas supply unit (not shown). The gas supply unit is identical to the gas supply unit, including the tubular cartridge housing and the gas cartridge, shown in FIGS. 1 through 4, and so will not be described again.

An axial bore 80 is formed in the cap 10a, and interconnects the threaded bore 24a with the outer face 32a of the cap 10a. The axial bore 80 has a reduced-diameter portion 82 towards the threaded bore, and an increased-diameter portion 84 towards the outer face 32a as shown. The puncture stem 16 is secured in the reduced-diameter portion 82 such that the proximal end of the puncture stem projects from the distal end of the threaded bore 24a by a predetermined amount.

A radial bore 86 is formed in the cap 10a to communicate with the axial bore 80. The exit tube 88 is secured in the radial bore. An intermediate portion 34a of the exit tube 88 has a narrowed diameter which serves as a flow restrictor. The flow restrictor limits the flow rate to approximately 3 liters/minute.

As can be seen in FIGS. 12 and 13, the cap in the second embodiment includes a control valve for controlling gas flow. The axial bore 80 provides the valve body, in which the valve shuttle 90 is slidably mounted. The valve shuttle 90, shown separately in FIGS. 14 and 15, has a closed button 92 which protrudes from the outer face 32a of the cap, an open bottom end 94 which remains inside the cap, and a radial hole 96.

The valve shuttle 90 is capable of moving axially between an on position, shown in FIG. 12, and an off position shown in FIG. 13, and is biased by the gas pressure towards the off position. When the shuttle 90 is in the on position, the radial hole 96 is aligned with the exit tube 88 as shown in FIG. 12. When the valve shuttle 90 is in its off position, the radial hole 96 is positioned away from the exit tube as shown in FIG. 13.

The valve shuttle 90 preferably slides in close contact with the axial bore 80 to prevent gas from escaping out of the outer face 32a of the cap 10a. An O-ring seal 98 is seated around the valve shuttle 90 to further safeguard against leakage. The valve shuttle 90 is retained within the axial bore 80 by the shouldered insert 100 secured in the increased-diameter portion 84.

A thumb lever 102 is mounted to the outer face 32a of the cap 10a by a hinge 104. The thumb lever 102 pivots on the hinge between an on position as shown in FIG. 12 to an off position as shown in FIG. 13. When the thumb lever 102 is in the off position, the valve shuttle 90 remains in its biased, off position. Moving the thumb lever 102 to its on position depresses the valve shuttle 90 into the on position by forcing down the button 92.

Referring to the second embodiment shown in FIG. 11, fitting 106 is mounted on the cap 10a at opening 108 and is adapted to receive an outlet line 36 adapted to be connected to an anesthesia assembly 38 and a pneumoneedle or Veress needle (not shown) as described above.

We claim:

1. An apparatus for inflating a body cavity with gas, the apparatus comprising:
    a source of insufflation gas;
    a container containing an anesthetic liquid; and
    a hollow tube in fluid communication with the source of insufflation gas and with the container, the hollow tube including atomization means for combining insufflation gas released from the source of insufflation gas into the hollow tube with anesthetic liquid from said container to form an atomized mist.

2. The apparatus of claim 1 further comprising a laparoscopic delivery device in fluid communication with the hollow tube, the delivery device having a tip proportioned for insertion through a laparoscopic incision and into a body cavity.

3. The apparatus of claim 1 wherein:
    the hollow tube has an exterior;
    the source of insufflation gas includes a cartridge containing compressed gas, the cartridge having an end with an opening sealed with a primary seal;
    the hollow tube includes a puncture tube connected thereto for puncturing the sealed opening and allowing gas to pass from the cartridge into the hollow tube; and
    the apparatus further comprises a secondary sealing means proximal to and operatively associated with the end of the cartridge for forming a seal in advance of puncturing the primary seal to prevent gas from escaping from the cartridge at the exterior of the hollow tube after the primary seal has been punctured by the puncturing means.

4. A method of inflating a body cavity with an anesthetic gas, comprising the steps of:
    (a) providing a source of insufflation gas and a source of anesthetic liquid;
    (b) forming a laparoscopic incision through body tissue to an underlying body cavity;
    (c) combining at least a portion of the insufflation gas and at least a portion of the anesthetic liquid to form an atomized mist; and
    (d) delivering the atomized mist into the body cavity via the laparoscopic incision.

5. The method of claim 4 wherein:
    step (a) includes the steps of providing:
        a cartridge containing compressed gas and having a sealed opening;
        a hollow tube having an exterior and a puncturing means for puncturing the sealed opening and allowing gas to pass from the cartridge into the hollow tube;
        a vial means for containing an anesthetic liquid;
        a spray means for combining the anesthetic liquid with the gas to form an atomized mist; and
        a secondary sealing means for preventing gas from escaping from the cartridge at the exterior of the hollow tube after the sealed opening has been punctured by the puncturing means.

6. The method of claim 5 wherein the method further includes the steps of:
    (e) before step (c), puncturing the sealed opening and allowing gas to pass from the cartridge into the hollow tube; and
    (f) after step (e), preventing gas from escaping from the cartridge at the exterior of the hollow tube using the secondary sealing means.

7. A portable apparatus for inflating a body cavity with gas, the apparatus comprising:
    a cartridge containing compressed gas, the cartridge having a sealed opening;
    a hollow tube having an exterior, the hollow tube including a puncturing means for puncturing the sealed opening and allowing gas to pass from the cartridge into the hollow tube and further including a vial means for containing an anesthetic liquid and a spray means for combining the anesthetic liquid with the gas to form an atomized mist; and
    a secondary sealing means for preventing gas from escaping from the cartridge at the exterior of the hollow tube after the sealed opening has been punctured by the puncturing means.

* * * * *